United States Patent [19]

Van Wijngaarden et al.

[11] Patent Number: 4,791,132
[45] Date of Patent: Dec. 13, 1988

[54] PHENYL, PYRROLIDIN-2-YL SUBSTITUTED PYRROLES HAVING ANTIPSYCHOTIC PROPERTIES

[75] Inventors: Ineke Van Wijngaarden; Cornelis G. Kruse; Roelof Van Hes; Johannes A. M. Van Der Heyden, all of Weesp, Netherlands

[73] Assignee: Duphar International Research B.V., Weesp, Netherlands

[21] Appl. No.: 94,746

[22] Filed: Sep. 9, 1987

[30] Foreign Application Priority Data

Sep. 12, 1986 [NL] Netherlands ................. 8602305

[51] Int. Cl.⁴ .................... A61K 31/40; C07D 207/30
[52] U.S. Cl. .................... 514/427; 548/374; 548/517; 548/518
[58] Field of Search ........... 548/336, 374, 517, 518; 514/397, 406, 424, 427

[56] References Cited

U.S. PATENT DOCUMENTS

| | | | |
|---|---|---|---|
| 4,219,560 | 8/1980 | Houlihan | 548/518 X |
| 4,321,385 | 3/1982 | Effland et al. | 548/518 X |
| 4,539,332 | 9/1985 | Biftu et al. | 548/518 X |

Primary Examiner—Richard A. Schwartz
Attorney, Agent, or Firm—Stevens, Davis, Miller & Mosher

[57] ABSTRACT

The invention relates to a group of new phenyl, pyrrolidin-2-yl substituted 5-ring heterocyclic compounds of the formula

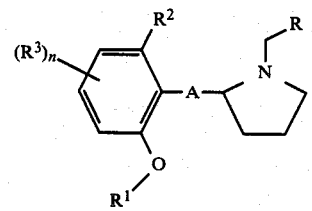

wherein A is an unsaturated heterocyclic 5-ring having at least one nitrogen or oxygen atom in the ring, with the proviso that the phenyl substituent is in a meta-position with respect to the 2-pyrrolidinyl substituent.

The compounds have interesting pharmacological, notably antipsychotic properties.

4 Claims, No Drawings

PHENYL, PYRROLIDIN-2-YL SUBSTITUTED PYRROLES HAVING ANTIPSYCHOTIC PROPERTIES

The invention relates to new phenyl, N-alkyl-pyrrolidin-2-yl substituted 5-ring heterocycles having interesting pharmacological, notably antipsychotic, properties, to the preparation of the said compounds, and to pharmaceutical compositions which comprise at least one of the said compounds, a salt or a derivative thereof as the active substance.

It was found that compounds of the general formula 1 wherein the symbols have the following meanings:

R is hydrogen, alkyl or a phenyl group optionally substituted with a group $R_3$;

$R_1$ is an alkyl group or alkenyl group which may form a ring with the adjoining C-atom of the phenyl group;

$R_2$ is hydrogen, hydroxy or alkoxy;

$R_3$ is alkyl, alkoxy, alkylthio, hydroxyl, amino, mono- or dialkylamino, alkylsulfonylamino, alkyl- or alkoxycarbonyl, nitro, cyano, halogen, trifluoromethyl, trifluoromethoxy or alkyl- or aminosulfonyl;

n is 0-3;

A is an unsaturated heterocyclic 5-ring having at least one nitrogen atom or oxygen atom in the ring, with the proviso that the phenyl substituent is in a meta-position with respect to the 2-pyrrolidinyl substituent;

and the acid addition salts and prodrugs thereof have interesting pharmacological, notably antipsychotic, properties.

The above-mentioned alkyl groups comprise 1-5 carbon atoms and may be straight or branched.

Halogen is preferably chlorine, or bromine.

Optionally present hydroxyl groups may be esterified.

Compounds which are to be preferred on the basis of their properties are compounds of formula 1, wherein R is methyl;

$R_1$ is methyl or ethyl;

$R_2$ is hydrogen;

$R_3$ is halogen, trifluoromethyl or alkylsulfonyl, and

A is a group of formula 2a, 2b or 2c;

(2a)    (2b)    (2c)

and the remaining symbols have the above-mentioned meanings.

Compounds according to the invention which are to be preferred in particular, are:

(a) 2-(2-methoxy-5-ethylsulfonylphenyl)-5-(N-ethyl-2-pyrrolidinyl)pyrrole;

(b) 2-(2-methoxy-3,5-dibromophenyl)-5-(N-ethyl-2-pyrrolidinyl)pyrrole.

Suitable acids with which the compounds according to the invention can form pharmaceutically acceptable acid addition salts are, for example, hydrochloric acid, sulphuric acid, phosphoric acid, nitric acid, and organic acids, for example, citric acid, fumaric acid, maleic acid, tartaric acid, acetic acid, benzoic acid, p-toluenesulfonic acid, methanesulfonic acid, naphtalenesulfonic acid, and the like.

Prodrugs are to be understood to include derivatives of the compounds of formula (1) which as such are inactive and which after administration to the body are converted into an active substance of formula 1.

Both racemates and the individual enantiomers belong to the invention.

A part of the compounds according to the invention have interesting psychotropic properties and are hence suitable for the treatment of affections and diseases which are the result of disturbances in the central nervous system. These compounds notably have a specific antipsychotic activity. In some compounds according to the invention, other properties may become prominent, for example, an antiaggressive, anticonvulsive, analgetic, antihypertensive, antiulcer or gastrokinetic activity.

The antipsychotic activity was determined in a test procedure in which the suppression of conditioned behaviour in experimental animals (rats) was measured in a manner known per se. The compounds were considered to be active when in this test they show at least 50% suppression of the conditioned behaviour after oral administration of 100 mg per kg of body weight or less.

The dopaminolytic properties of the compounds were determined in mice by means of a test procedure in which the extent of inhibition was established of behaviour (climbing behaviour) which is induced by the dopamine agonist apomorphine. A compound is considered to be active when after oral administration of dosages smaller than 50 mg/kg an inhibition of more than 50% is found.

In addition to the above-described in vivo tests, in vitro receptor binding experiments were also carried out by means of radioactive labelled ligands in brain tissue homogenates. In this manner very high affinities of the preferred compounds were found (expressed in $K_i$ values less than 100 nM) for dopamine receptors.

In contrast with the greater part of the dopaminolytics used in the clinic so far, for example haloperidol and tricyclic compounds such as chloropromazine and clozapine, said affinity depends on the presence of sodium ions. When performing the experiments as described in Eur. J. Pharmacol. 46 (1977), p. 377, Na ratios were found of a value from 10 to 50. The affinity for other neurotransmitter-receptor types, for example, cholinergic, adrenergic and serotonergic receptors, were very low.

These pharmacological data indicate an interesting clinical pattern of the compounds, in that sense that the antipsychotic activity is not associated with the occurrence of side effects which are characteristic of nearly all the neuroleptics used so far.

The quantity, frequency and way of administration may differ for each individual case, also depending on the nature and the severity of the disturbances. In general, a dosage of 5–500 mg daily, and preferably 5–100 mg daily, preferably in one dosage a day, may be used for humane application.

The active compounds according to the invention and their salts and prodrug forms may be processed to compositions by means of standard techniques known per se, for example, pills, tablets, coated tablets, capsules, powders, injection liquids and the like, while using the conventional auxiliary substances, for example, solid and liquid carrier materials.

The compounds and their acid addition salts, prodrugs and enantiomers may be transformed into a form of administration suitable for use in known manner.

The new compounds according to the invention may be prepared in a manner known for the synthesis of analogous compounds.

A suitabale method of preparing the compounds of formula 1 consists of a condensation reaction of a compound of formula 3 with a pyrrolidone derivative of formula 4

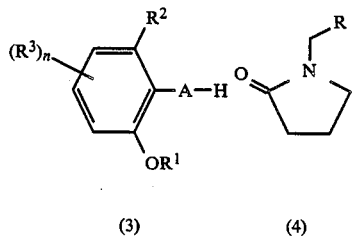

(3)    (4)

wherein the symbols have the meanings given hereinbefore. This coupling is carried out in three steps. First, a strong electrophilic reagent is made from 4 under the influence of an activating reagent from the group of Lewis acids, for example, phosphoric acid trichloride, aluminium trichloride or ferrichloride, boron trifluoride, stannic tetrachloride or an equivalent reagent, which then performs an aromatic substitution reaction on the aromatic 5-ring A of the compound of formula 3. Suitable solvents for these reactions are chlorinated hydrocarbons, for example, dichloromethane, chloroform, and 1,2-dichloroethane. Aromatic solvents, for example, benzene, toluene or chlorobenzene may also be used. Depending on the reactivity of A, the temperature is between −20° C. and the reflux temperature of the solvent used. In the third step a reducing agent is added from the group of alkali metal borohydride or alkali metal aluminum hydrides, for example, sodium borohydride., The starting compounds of formula 3 can be obtained by means of cyclization reactions known per se. If A is a 2-substituted pyrrole ring or furan ring, said cyclization occurs with the corresponding 1,4-dicarbonyl compounds, as described in Monatshefte für Chemie 108 (1977), p. 285. If A is a 1-substituted pyrazole ring, the corresponding arylhydrazine is treated with malonic dialdehyde tetramethylacetal, as described in British Patent Specification No. 797,144, Chem. Abstr. 53, (1959), 4983i.

When the groups $R_2$ or $R_3$ in formula 1 are a hydroxyl group, such compounds can also be obtained by splitting off, as the last reaction step, a protective group from the corresponding compounds of formula 1. Other chemical conversions within the meanings of R and $R_1$–$R_3$, for example reduction reactions, may also be used as the last reaction step.

The invention will now be described in greater detail with reference to the following specific examples.

EXAMPLE I 2-(2-methoxy-5-ethylsulfonylphenyl)-5-(N-ethyl-2-pyrrolidinyl)pyrrole.

The reaction is carried out under an atmosphere of dry nitrogen. 3 mMol of phosphoric acid trichloride (0.27 ml) are added dropwise in 10 minutes to 340 mg (3 mMol) of N-ethylpyrrolidone-2. After stirring for 15 minutes at room temperature, 5 ml of 1,2-dichloroethane are added. The solution is cooled to 0° C., after which a solution of 3 mMol (795 mg) of 2-(2-methoxy-5-ethylsulfonylphenyl)pyrrole in 9 ml of 1,2-dichloroethane is added dropwise in approximately 20 minutes. The reaction mixture is stirred for 16 hours at room temperature, then cooled to 0° C. and 1.0 g of sodium borohydride is then added. After stirring at room temperature for two hours, the mixture is cooled again to 0° C. and first 5 ml of methanol and 30 ml of water are then added slowly. After stirring at room temperature for 1 hour, the reaction mixture is extracted with dichloromethane (3×15 ml). The organic layer is dried on magnesium sulfate and is then concentrated in vacuo. 1.2 g Of a yellow oil are obtained. After chromatography over a silicagel column with dichloromethane containing 3% methanol and dichloromethane containing 15% methanol, respectively, 2-(2-methoxy-5-ethylsulfonylphenyl)-5-(N-ethyl-2-pyrrolidinyl)pyrrole is obtained in a yield of 600 mg (yield 55%) as a light-brown powder having a melting-point of 45° C.

EXAMPLE II 2-(2-methoxy-3,5-dibromophenyl)-5-(N-ethyl-2-pyrrolidinyl)pyrrole.

The above compound was obtained in a manner identical to that described in EXAMPLE I, starting from 2-(2-methoxy-3,5-dibromophenyl)pyrrole. The pure product, after column chromatography, is an oil.

The proton-NMR data of the compounds of EXAMPLES I and II were in full agreement with the expected structure.

We claim:

1. A compound of formula 1,

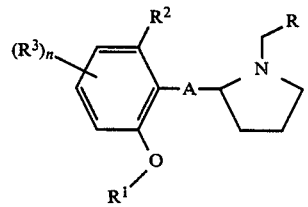

wherein:
R is hydrogen or alkyl having 1–3 carbon atoms;
$R_1$ is straight or branched alkyl having 1–4 carbon atoms;
$R_2$ is hydrogen;
$R_3$ is halogen or alkyl sulfonyl having 1–3 carbon atoms;
n is 0–2;

A is pyrrole, with the proviso that the phenyl substituent is in a meta-position with respect to the 2-pyrrolidinyl substituent;

or an acid addition salt or prodrug thereof.

2. A compound as claimed in claim 1, wherein R is methyl R₁ is methyl or ethyl, R₂ is hydrogen, R₃ is halogen or alkylsulfonyl, A is a group of the formula 2a

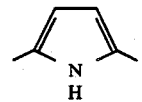
(2a)

and n has the meanings given in claim 1, or an acid addition salt or prodrug thereof.

3. A compound as claimed in claim 1;
(a) 2-(2-methoxy-5-ethylsulfonylphenyl)-5-(N-ethyl-2-pyrrolidinyl)pyrrole;
(b) 2-(2-methoxy-3,5-dibromophenyl)-5-(N-ethyl-2-pyrrolidinyl)pyrrole;

or an acid addition salt or prodrug thereof.

4. A pharmaceutical composition having antipsychotic activity which comprises an effective amount of at least one compound according to claim 1 as the active component and a suitable carrier.

* * * * *